(12) United States Patent
Tan et al.

(10) Patent No.: US 12,232,703 B2
(45) Date of Patent: Feb. 25, 2025

(54) SYSTEM AND METHOD FOR OPERATING A URETEROSCOPE IRRIGATION DEVICE

(71) Applicant: University Health Network, Toronto (CA)

(72) Inventors: Guan Hee Tan, Toronto (CA); Nathan Perlis, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 383 days.

(21) Appl. No.: 17/065,690

(22) Filed: Oct. 8, 2020

(65) Prior Publication Data

US 2021/0100436 A1  Apr. 8, 2021

Related U.S. Application Data

(60) Provisional application No. 62/912,166, filed on Oct. 8, 2019.

(51) Int. Cl.
| | | |
|---|---|---|
| *A61B 1/015* | (2006.01) | |
| *A61B 1/00* | (2006.01) | |
| *A61B 1/018* | (2006.01) | |
| *A61B 1/307* | (2006.01) | |
| *A61B 17/00* | (2006.01) | |
| *A61B 18/22* | (2006.01) | |

(52) U.S. Cl.
CPC .......... *A61B 1/015* (2013.01); *A61B 1/00068* (2013.01); *A61B 1/018* (2013.01); *A61B 1/307* (2013.01); *A61B 17/00234* (2013.01); *A61B 18/22* (2013.01); *A61B 2017/0034* (2013.01); *A61B 2017/00358* (2013.01)

(58) Field of Classification Search
CPC .......... A61B 1/303; A61B 1/307; A61B 1/12; A61B 1/126; A61B 1/127; A61B 1/128; A61B 1/015; A61B 1/00128; A61B 1/00119; A61B 1/00112; A61B 1/00091; A61B 1/00094; A61B 1/00066; A61B 1/00068; A61M 3/0262
See application file for complete search history.

(56) References Cited

U.S. PATENT DOCUMENTS

| | | | | |
|---|---|---|---|---|
| 3,730,645 | A | * | 5/1973 | Mashakaru ........ A61B 1/00121 417/313 |
| D284,028 | S | * | 5/1986 | Seager .......................... D24/138 |
| 4,598,698 | A | * | 7/1986 | Siegmund ................ A61B 1/12 600/156 |
| 6,620,132 | B1 | * | 9/2003 | Skow .................... A61M 27/00 604/142 |
| 9,050,036 | B2 | * | 6/2015 | Poll ........................ A61B 1/313 |
| 10,220,123 | B2 | * | 3/2019 | Monty .................. A61M 1/742 |
| 10,286,141 | B2 | * | 5/2019 | Monty .................. A61M 1/7411 |
| 10,702,636 | B2 | * | 7/2020 | Cheng ............. A61B 17/32002 |
| 2005/0025646 | A1 | | 2/2005 | Miller et al. |
| 2007/0213668 | A1 | * | 9/2007 | Spitz ..................... A61M 3/022 604/131 |

(Continued)

*Primary Examiner* — Ryan N Henderson
(74) *Attorney, Agent, or Firm* — Quarles & Brady, LLP

(57) ABSTRACT

An irrigation device is integrated into a ureteroscope housing. The surgeon can increase flow of irrigation fluid by squeezing a compressible chamber of the irrigation device with the same hand used to hold the ureteroscope housing. A standard fluid bag and tubing can deliver irrigation fluid to the irrigation device.

18 Claims, 2 Drawing Sheets

(56) References Cited

U.S. PATENT DOCUMENTS

| | | | |
|---|---|---|---|
| 2008/0319266 A1* | 12/2008 | Poll | A61B 1/313 600/157 |
| 2012/0101337 A1* | 4/2012 | Clark | A61B 1/00091 600/157 |
| 2012/0165610 A1* | 6/2012 | Poll | A61B 17/3421 600/157 |
| 2013/0165849 A1* | 6/2013 | Monty | A61M 3/0283 604/181 |
| 2014/0371763 A1* | 12/2014 | Poll | A61B 34/30 606/130 |
| 2022/0133980 A1* | 5/2022 | Lobo | A61M 1/774 604/30 |

\* cited by examiner

SYSTEM AND METHOD FOR OPERATING A URETEROSCOPE IRRIGATION DEVICE

CROSS-REFERENCE TO RELATED APPLICATIONS

This application claims the benefit of U.S. Provisional Patent Application Ser. No. 62/912,166, filed on Oct. 8, 2019, and entitled "SYSTEM AND METHOD FOR OPERATING A URETEROSCOPE IRRIGATION DEVICE," which is herein incorporated by reference in its entirety.

BACKGROUND OF THE INVENTION

The flexible ureteroscope is commonly used to treat diseases of the upper urinary tract, such as renal stones and urothelial cancer. During a ureteroscopy procedure, steady flow of irrigation fluid through the scope is needed to maintain a clear view of the surgical field. Occasionally, bleeding or debris might reduce visual clarity. In these instances, a short period of increased flow would usually be required to wash away the bleeding or debris, thus restoring optimal vision.

Increasing the flow of irrigation fluid can be attained in several ways. Commonly, the fluid container is squeezed manually or with a pressurized bag wrapped around it. However, this maneuver not only requires an assistant to be constantly available, but the assistant must also coordinate well with the surgeon regarding when increased flow is required.

There are a few other ways the surgeon could be in control of the irrigation flow. One is by using a motorized mechanical pump, in which the surgeon controls the flow by adjusting the tap on the scope. This system is expensive and the flow could sometimes be too forceful, which might lead to increased pressure in the renal system. Prolonged periods of high pressure within the renal system could also be associated with urosepsis.

Another solution is to have the surgeon squeeze or step on a pump that propels the irrigation fluid through the scope. In this hand-pump setup, the surgeon would have to free up a hand to squeeze a hand-pump that is separate from the ureteroscope. Usually the hand that the surgeon needs to free up to use the hand-pump is the hand that is already preoccupied with manipulating a guidewire, endoscopic basket, or laser fiber. Similarly, the foot-pump has the drawback that it requires the surgeon to take his or her foot off the laser pedal to work the irrigation pump. Both of these systems are not ideal because they take the surgeon's attention away from focusing on the stone or tumor that is being treated.

It would be ideal if the surgeon were able to regulate the flow of irrigation fluid without disrupting any ongoing task that is being performed.

SUMMARY OF THE INVENTION

It is an aspect of the present disclosure to provide a ureteroscope that generally includes a housing having a proximal end and a distal end, a compressible chamber composed of a flexible material and coupled to an outer surface of the housing, and a working channel. The compressible chamber has an inlet arranged adjacent the proximal end of the housing and an outlet arranged adjacent the distal end of the housing. The inlet is configured to receive fluid and communicate the fluid into the compressible chamber. The working channel is coupled to the distal end of the housing and is in fluid communication with the outlet of the compressible chamber. When the compressible chamber is compressed, fluid contained in the compressible chamber is forced out of the compressible chamber and into the working channel through the outlet.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION OF THE INVENTION

Described herein are systems and methods for operating a ureteroscope irrigation device. Embodiments of a ureteroscopy system described in the present disclosure facilitate the control of multiple surgical instruments by a medical provider during a ureteroscopy procedure, while allowing the medical provider to control irrigation. The present disclosure provides an improved ureteroscope device in which an irrigation device is integrated with the ureteroscope housing. This ureteroscopy system allows for the surgeon's working hand and feet to remain free from the extra task of regulating irrigation flow with a separate device, thereby alleviating the drawbacks of previous systems for irrigation control during a ureteroscopy procedure.

Figure 1:
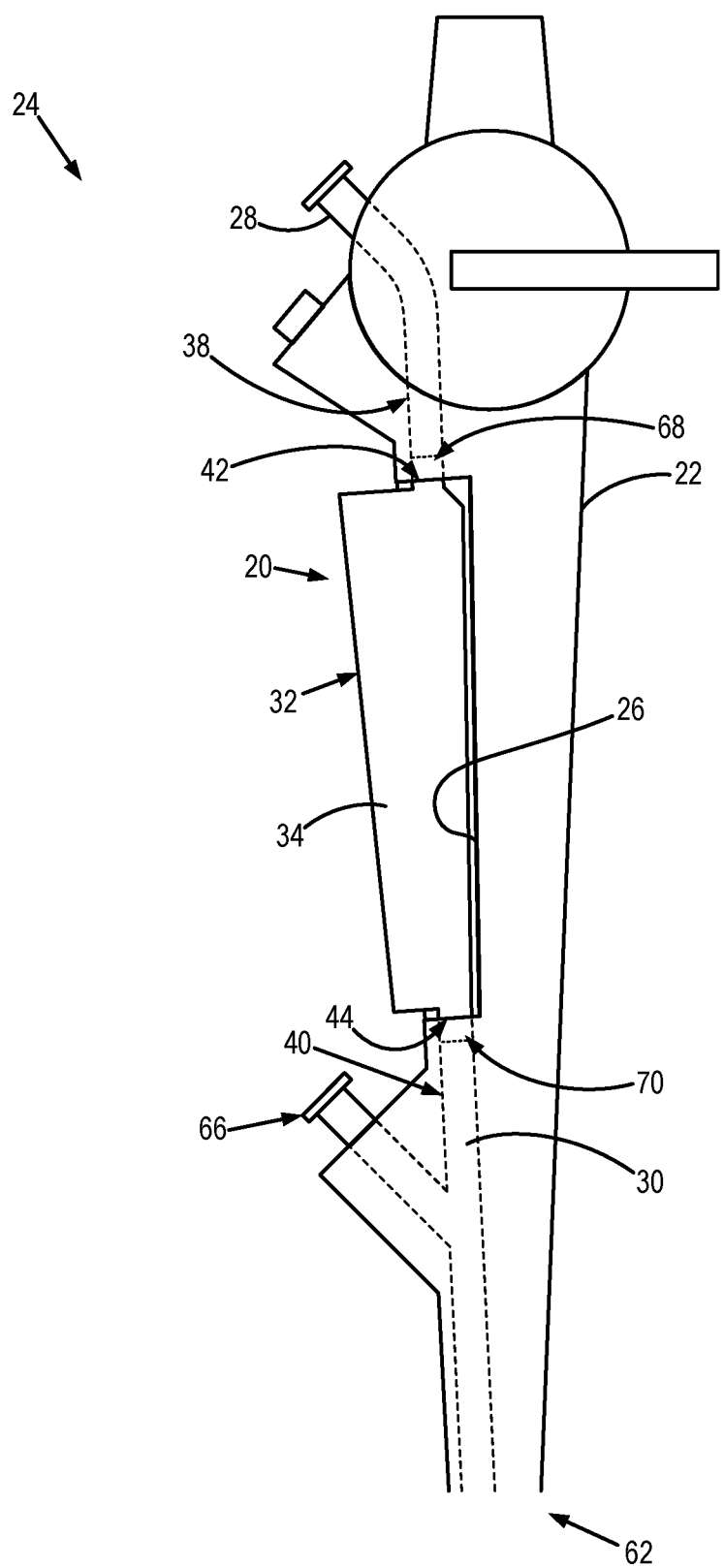
FIG. 1 is a partial side of a ureteroscope according to the disclosure with some parts rendered transparently for clarity.

Referring first to FIG. 1, an irrigation device 20 coupled to a housing 22 of a ureteroscope 24 according to the disclosure is illustrated. The housing 22 forms a handpiece that is configured to be held in the hand of a medical provider. The housing 22 includes a recess (or gap) 26 that is sized and shaped to receive the irrigation device 20. The irrigation device 20 can be a removable or replaceable module that is installed into the housing 22. Alternatively, the irrigation device 20 can be integrally formed with the housing 22.

The irrigation device 20 includes an inlet 28, an outlet 30, and a body 32. The body 32 comprises a compressible chamber 34 that is formed of a flexible material having sufficient resilience such that when the compressible chamber 34 is compressed fluid contained within the compressible chamber 34 will be forced out of the compressible chamber 34 and through the outlet 30. As one non-limiting example, the compressible chamber 34 can be composed of a polyvinyl chloride ("PVC"). In other examples, the compressible chamber 34 can be composed of other flexible materials, such as other flexible polymer materials. For instance, the compressible chamber 34 may be composed of low-density polyethylene ("LDPE"), high-density polyethylene ("HDPE"), polypropylene, and the like. After compression, the compressible chamber 34 will return to its initial shape, thereby drawing fluid back into the compressible chamber 34 through the inlet 28. In this way, the compressible chamber 34 serves as a hand-pump for the medical provider. The recess 26 is formed into the housing 22 so that when the irrigation device 20 is installed, the medical provider's fingers naturally extend and/or wrap around the body 32 of the compressible chamber 34.

The body 32 can be shaped to provide ergonomic benefit to users of the irrigation device 20 during a ureteroscopy procedure. For example, in some forms, the body 32 and/or the compressible chamber 34 is cylindrical in shape. As one non-limiting example, the compressible chamber 34 can have a circular cylindrical shape (or other cylindrical shape); though, in other configurations the compressible chamber 34 can have an otherwise regular or non-regular shape. In general, the compressible chamber 34 is preferable shaped to have an outer surface that can be comfortably or otherwise ergonomically received by the medical provider's hand. As a non-limiting example, the body 32 can be 15 cm long and can have a 2.5 cm diameter.

In one example construction, the wall thickness of the compressible chamber 34 can be about 5 mm or thinner. In general, the wall thickness will depend on the material used for constructing the compressible chamber 34. Particularly, the wall thickness can be made thinner provided the selected material retains sufficient flexibility and resilience to allow for the compressible chamber 34 to be easily compressed by the medical provider, and such that the compressible chamber 34 will return to its initial shape and/or volume upon cessation of the applied compression. In certain non-limiting examples, the wall thickness of the compressible chamber 34 can be in a range from about 0.1 mm to about 5 mm, from about 0.5 mm to about 4 mm, from about 1 mm to about 3 mm, or from about 2 mm to 3 mm. In other non-limiting examples, the wall thickness of the compressible chamber 34 may be in a range from 0.2 mm to 1 mm, from 0.25 mm to 0.8 mm, or from 0.4 mm to 0.6 mm. The ureteroscope housing 22 is formed of a rigid material that is capable of providing counter-resistance when the compressible chamber 34 is compressed.

The inlet 28, the outlet 30, and the compressible chamber 34 are all in fluid communication with a fluid reservoir 36 (shown in FIG. 2), which contains fluid to be used for irrigation and has a reservoir tube 46 extending from the fluid reservoir 36 to the ureteroscope 24. The housing 22 can include an inlet conduit 38 and an outlet conduit 40 to which the inlet 28 and the outlet 30, respectively, are coupled. In some forms, the inlet 28 can be coupled to the base 42 of the inlet conduit 38, so that the inlet conduit 38 is what mechanically and fluidly connects the inlet 28 to the reservoir tube 46.

In some forms, the inlet 28 is formed as a tube that extends upward through the inlet conduit 38 in the housing 22. The inlet 28 can include a Luer lock fitting or another mechanical coupling capable of securing and fluidly coupling the reservoir tube 46 extending from the fluid reservoir 36 to the inlet 28. The outlet 30 can be coupled to the outlet conduit 40, such as at the top 44 end of the outlet conduit 40. The inlet 28 and outlet 30 can be manufactured from PVC or any other suitable medically acceptable plastic or polymer material. It is contemplated that the irrigation device 20 may be mechanically coupled to the housing 22 by any of the inlet 28, the outlet 30, or the body 32.

Figure 2:
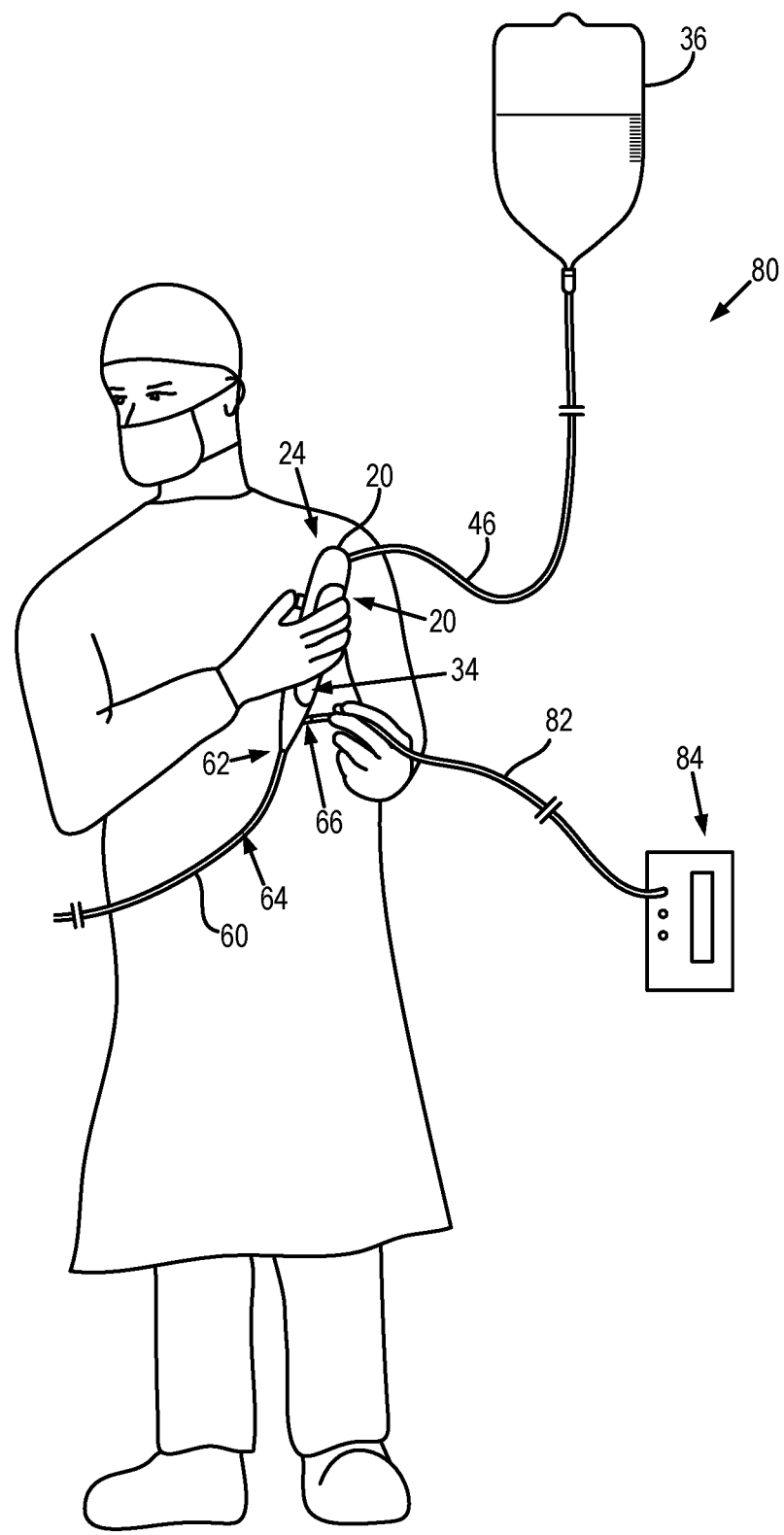
FIG. 2 is a front view of the ureteroscope of FIG. 1 in use by a medical provider in a ureteroscopy system according to the disclosure.

Referring to FIGS. 1 and 2, the ureteroscope 24 includes a flexible tube 60 that is coupled to a distal end 62 of the housing 22. The flexible tube 60 contains a working channel 64 that extends through the flexible tube 60 and can accommodate a variety of surgical instruments, such as a guidewire, an endoscopic basket, or laser fiber, among others. The flexible tube 60 can also house fiber optic or electrical elements for visual transmission, mechanical cables that control movement of the distal tip, and so on. Surgical instruments can be inserted into the working channel 64 via one or more ports 66 in the ureteroscope housing 22. The working channel 64 is in fluid communication with the outlet 30, the compressible chamber 34, the inlet 28, and the fluid reservoir 36. In this way, irrigation fluid can flow along a fluid path starting from the fluid reservoir 36, through the inlet 28, through the compressible chamber 34, through the outlet 30 into the working channel 64, and out of a distal tip of the working channel 64 into the body of a patient.

In some embodiments, one or more one-way valves are positioned along the fluid path between the fluid reservoir 36 and the distal tip of the working channel 64 to prevent backflow. The one-way valves may include duckbill valves, ball check valves, cross-slit valves, diaphragm check valves, or other suitable one-way valve designs that allow for forward flow while preventing backflow. For example, a first one-way valve 68 can be positioned between the inlet 28 and the compressible chamber 34 to prevent backflow from the compressible chamber 34 to the fluid reservoir 36 when pressure is applied to the compressible chamber 34 in order to force the fluid through the working channel 64 (or separate irrigation channel). In one example configuration, the first one-way valve 68 may be coupled (e.g., fluidically coupled) to the inlet 28. For instance, the first one-way valve 68 may be coupled to the inlet 28 at or near the base 42 end of the inlet conduit 38 (i.e., adjacent the compressible chamber 34). In one configuration, the first one-way valve 68 may be arranged within the inlet conduit 38 adjacent the compressible chamber 34, such that the inlet 28 can be introduced into the inlet conduit 38 and mated or otherwise coupled to the first one-way valve 68.

As another example, a second one-way valve 70 can be positioned between the outlet 30 and the compressible chamber 34 to prevent backflow from and/or between the distal tip of the working channel 64 (or separate irrigation channel) and the compressible chamber 34. For instance, the second one-way valve 70 can prevent air from being sucked into the working channel 64 (or separate irrigation channel), which would result in no fluid flush, or only partial fluid flush, with the next compression. Additionally, the second one-way valve 70 helps create suction force to refill the compressible chamber 34 from the fluid reservoir 36 when pressure on the compressible chamber 34 is released. In one example configuration, the second one-way valve 70 may be coupled (e.g., fluidically coupled) to the outlet 30. For instance, the second one-way valve 70 may be coupled to the outlet 30 at or near the top 44 end of the outlet conduit 40 (i.e., adjacent the compressible chamber 34). In one configuration, the second one-way valve 70 may be arranged within the outlet conduit 40 adjacent the compressible chamber 34, such that the outlet 30 can be introduced into the outlet conduit 40 and mated or otherwise coupled to the second one-way valve 70.

In some forms, an irrigation lumen or other tubing is provided that runs through the working channel 64 and is fluidly coupled to the fluid reservoir 36. In this way, irrigation fluid only flows through the irrigation lumen. The configuration having an irrigation lumen allows the fluid flowing through the irrigation lumen to be hermetically separated from the interior volume of the working channel 64, such that other instruments extending through the working channel 64 are not introduced into the irrigation fluid path during a ureteroscopy procedure.

FIG. 2 illustrates a surgeon using a ureteroscopy system 80 according to the present disclosure. The ureteroscopy system 80 includes the ureteroscope 24 having the irrigation device 20, a laser fiber 82, a laser generator 84, and the fluid reservoir 36. The fluid reservoir 36 can be, for example, a standard bag used for intravenous infusion of fluid for medical purposes. In use, the fluid reservoir 36 is elevated above the patient to allow the irrigation fluid to flow down continuously by gravity. In one non-limiting example, the fluid reservoir 36 can be elevated above the patient by about 70 cm. More generally, the fluid reservoir 36 can be elevated to a height that allows for sufficient pressure to fill the compressible chamber 34 in a clinically relevant time, to ensure the fluid reservoir 36 does not interfere with the medical provider or their line of sight, or combinations of these and other factors. The irrigation fluid is supplied from the fluid reservoir 36 through the reservoir tube 46 into the compressible chamber 34. When a greater flow is required, the surgeon can squeeze the compressible chamber 34 while holding the ureteroscope housing 22. By squeezing the compressible chamber 34, irrigation fluid is propelled out the distal tip of the working channel 64. Thus, irrigation can be provided without the medical provider needing to use their contralateral hand or their feet, which could be involved with performing other tasks such as operating the laser generator 84. In FIG. 2, the surgeon's left hand is handling the laser fiber 82, which is attached to a laser generator 84. The ureteroscopy system 80 provides advantages over conventional systems that do not have an irrigation device 20 which is ergonomically integrated into the ureteroscope 24.

The present invention has been described in terms of one or more preferred embodiments, and it should be appreciated that many equivalents, alternatives, variations, and modifications, aside from those expressly stated, are possible and within the scope of the invention.

The invention claimed is:

1. A ureteroscope comprising:
a housing having a proximal end and a distal end;
a compressible chamber composed of a flexible material and coupled to an outer surface of the housing, the compressible chamber having an inlet arranged adjacent the proximal end of the housing and an outlet arranged adjacent the distal end of the housing, wherein the inlet is configured to receive fluid and communicate the fluid into the compressible chamber;
a working channel coupled to the distal end of the housing and in fluid communication with the outlet of the compressible chamber, wherein the working channel is axially aligned with the outlet of the compressible chamber, wherein the working channel includes an interior volume configured to receive a surgical instrument;
a flexible tube coupled to the distal end of the housing that contains the working channel; and
a port disposed on an exterior of the housing, distal from the compressible chamber, and configured to receive the surgical instrument for insertion of the surgical instrument through the working channel from the housing through the flexible tube;
wherein when the compressible chamber is compressed, the fluid contained in the compressible chamber is forced out of the compressible chamber through the outlet and into the interior volume of the working channel.

2. The ureteroscope as recited in claim 1, wherein the housing has formed therein a recess that is sized and shaped to receive the compressible chamber so as to couple the compressible chamber to the outer surface of the housing.

3. The ureteroscope as recited in claim 1, wherein the compressible chamber is coupled to the housing.

4. The ureteroscope as recited in claim 1, wherein the compressible chamber is integrally formed as a part of the housing.

5. The ureteroscope as recited in claim 1, wherein the compressible chamber is composed of a flexible material having sufficient resilience such that after compressing the compressible chamber, the compressible chamber returns to its initial shape and draws fluid into the compressible chamber through the inlet.

6. The ureteroscope as recited in claim 1, wherein the compressible chamber has a cylindrical shape.

7. The ureteroscope as recited in claim 6, wherein the compressible chamber has a length of 15 cm and a diameter of 2.5 cm.

8. The ureteroscope as recited in claim 1, wherein the compressible chamber has a thickness in a range of 0.1 mm to 5 mm.

9. The ureteroscope as recited in claim 1, wherein the housing is composed of a rigid material that provides counter resistance when the compressible chamber is compressed.

10. The ureteroscope as recited in claim 1, wherein the housing comprises a handpiece shaped to accommodate a user's hand such that the user's hand extends and wraps around the compressible chamber when holding the housing.

11. The ureteroscope as recited in claim 1, further comprising a one-way valve fluidically coupled to the inlet of the compressible chamber in order to prevent backflow of fluid from the compressible chamber into the inlet.

12. The ureteroscope as recited in claim 11, wherein the one-way valve is arranged between the inlet and the compressible chamber.

13. The ureteroscope as recited in claim 1, further comprising a one-way valve fluidically coupled to the outlet of the compressible chamber in order to prevent backflow of fluid from the outlet into the compressible chamber.

14. The ureteroscope as recited in claim 13, wherein the one-way valve is arranged between the outlet and the compressible chamber.

15. The ureteroscope as recited in claim 1, further comprising:
a first one-way valve fluidically coupled to the inlet of the compressible chamber in order to prevent backflow of fluid from the compressible chamber into the inlet; and
a second one-way valve fluidically coupled to the outlet of the compressible chamber in order to prevent backflow of fluid from the outlet into the compressible chamber.

16. The ureteroscope as recited in claim 15, wherein the first one-way valve is arranged between the inlet and the compressible chamber, and the second one-way valve is arranged between the outlet and the compressible chamber.

17. The ureteroscope as recited in claim 1, further comprising a port arranged adjacent the distal end of the housing and in communication with the working channel, the port being configured to accommodate a surgical instrument.

18. The ureteroscope as recited in claim 17, wherein the port is sized and shaped to accommodate a surgical instrument comprising at least one of a guidewire, an endoscopic basket, or a laser fiber.

* * * * *